(12) United States Patent
Gandhi et al.

(10) Patent No.: US 11,103,847 B2
(45) Date of Patent: *Aug. 31, 2021

(54) REACTOR FOR PRODUCING PHARMACEUTICAL PARTICLES IN A PRECIPITATION PROCESS

(71) Applicant: MannKind Corporation, Westlake Village, CA (US)

(72) Inventors: Sanket Gandhi, Danbury, CT (US); Karen Moraleda, New Fairfield, CT (US); Jadwiga Jachowicz, Bethel, CT (US); Michael Zupon, Basking Ridge, NJ (US)

(73) Assignee: MannKind Corporation, Westlake Village, CA (US)

( * ) Notice: Subject to any disclaimer, the term of this patent is extended or adjusted under 35 U.S.C. 154(b) by 764 days.

This patent is subject to a terminal disclaimer.

(21) Appl. No.: 15/913,993

(22) Filed: Mar. 7, 2018

(65) Prior Publication Data

US 2018/0193813 A1 Jul. 12, 2018

Related U.S. Application Data

(60) Division of application No. 13/936,463, filed on Jul. 8, 2013, now abandoned, which is a continuation of
(Continued)

(51) Int. Cl.
  *B01J 19/00* (2006.01)
  *B01F 7/00* (2006.01)

(52) U.S. Cl.
  CPC ....... *B01J 19/0066* (2013.01); *B01F 7/00766* (2013.01)

(58) Field of Classification Search
  CPC .......................... B01J 19/0066; B01F 7/00766
  (Continued)

(56) References Cited

U.S. PATENT DOCUMENTS 3,744,763 A 7/1973 Schnoring et al.
5,352,461 A 10/1994 Feldstein et al.
(Continued)

FOREIGN PATENT DOCUMENTS

CA 2033805 C 8/1991
CN 1571691 A 1/2005
(Continued)

OTHER PUBLICATIONS

International Search Report and Written Opinion dated Jan. 11, 2011 from corresponding International Application No. PCT/US2010/055090.
(Continued)

*Primary Examiner* — Marc C Howell
(74) *Attorney, Agent, or Firm* — Wolf, Greenfield & Sacks, P.C.

(57) ABSTRACT

Reactors, reactor systems and methods for producing particles in a precipitation process are provided. The reactor includes a housing defining a reaction chamber, a stator assembly including two or more stators, a rotor assembly including two or more rotors, the rotor assembly configured for rotation about an axis of rotation relative to the stator assembly, a first inlet to supply a first reactant material to the reaction chamber at a first radial location, a second inlet to supply a second reactant material to the reaction chamber at a second radial location different from the first radial location, wherein the first and second reactant materials react to produce precipitation of particles in the reaction chamber, and an outlet to supply the particles formed in the reaction chamber.

8 Claims, 8 Drawing Sheets

Related U.S. Application Data application No. 12/917,611, filed on Nov. 2, 2010, now Pat. No. 8,491,848.

(60) Provisional application No. 61/384,662, filed on Sep. 20, 2010, provisional application No. 61/257,311, filed on Nov. 2, 2009.

(58) Field of Classification Search
USPC .......................................................... 366/302
See application file for complete search history.

(56) References Cited

U.S. PATENT DOCUMENTS

| | | | |
|---|---|---|---|
| 5,427,992 A * | 6/1995 | Graefe | B01J 19/1881 502/111 |
| 5,503,852 A | 4/1996 | Steiner et al. | |
| 5,590,961 A * | 1/1997 | Rasmussen | B01F 7/00758 366/165.1 |
| 6,024,481 A | 2/2000 | Hillström et al. | |
| 6,071,497 A | 6/2000 | Steiner et al. | |
| 6,331,318 B1 | 12/2001 | Milstein | |
| 6,444,226 B1 | 9/2002 | Steiner et al. | |
| 6,471,392 B1 | 10/2002 | Holl et al. | |
| 7,052,172 B2 | 5/2006 | Jahn et al. | |
| 7,166,260 B2 | 1/2007 | Shih et al. | |
| 7,709,639 B2 | 5/2010 | Stevenson et al. | |
| 7,964,059 B2 | 6/2011 | Peters et al. | |
| 8,491,848 B2 | 7/2013 | Gandhi et al. | |
| 2003/0152500 A1 | 8/2003 | Dalziel et al. | |
| 2004/0187770 A1 | 9/2004 | Calabrese et al. | |
| 2005/0202095 A1* | 9/2005 | Daiziel | B01D 9/005 424/489 |
| 2007/0059374 A1 | 3/2007 | Hokenson et al. | |
| 2007/0125499 A1* | 6/2007 | Peters | B01D 1/30 159/49 |
| 2009/0110647 A1 | 4/2009 | Richardson | |
| 2011/0105719 A1 | 5/2011 | Gandhi et al. | |
| 2013/0296566 A1 | 11/2013 | Gandhi et al. | |

FOREIGN PATENT DOCUMENTS

| | | |
|---|---|---|
| CN | 101027057 A | 8/2007 |
| DE | 30 09 233 A1 | 9/1981 |
| DE | 36 11 048 A1 | 10/1987 |
| EP | 0 442 300 A2 | 8/1991 |
| EP | 1 790 615 A1 | 5/2007 |
| GB | 2 308 076 A | 6/1997 |
| JP | 02-144136 A2 | 6/1990 |
| JP | 08-504663 | 5/1996 |
| JP | 08-141378 A2 | 6/1996 |
| JP | 10-226981 A2 | 8/1998 |
| JP | 2005-506174 A | 3/2005 |
| KR | 10-2008-0043387 A | 5/2008 |
| RU | 2021006 C1 | 10/1994 |
| RU | 2144423 C1 | 1/2000 |
| RU | 2166987 C1 | 5/2001 |
| RU | 2357791 C1 | 6/2009 |
| UA | 64606 C2 | 2/2004 |
| WO | WO 94/13395 A1 | 6/1994 |
| WO | WO 2008/077116 A2 | 6/2008 |
| WO | WO 2009/055740 A2 | 4/2009 |
| WO | WO 2009/055742 A2 | 4/2009 |

OTHER PUBLICATIONS

International Preliminary Report on Patentability dated May 18, 2012 from corresponding International Application No. PCT/US2010/055090.
European Search Report dated Nov. 17, 2015 from corresponding European Application No. 10827641.1.
Australian Examination Report dated May 20, 2016 from corresponding Australian Patent Application No. 2015203301.
Canadian Examiner's Report dated Jul. 20, 2016 from corresponding Canadian Patent Application No. 2,779,614.
Chinese Office Action and Search Report dated Jan. 6, 2014 from corresponding Chinese Patent Application No. 201080049599.8.
Chinese Office Action dated Aug. 16, 2016 from corresponding Chinese Application No. 201510102962.2.
Japanese Office Action dated Jan. 6, 2015 from corresponding Japanese Application No. 2012-537189.
Korean Office Action dated Mar. 6, 2017 from corresponding Korean Application No. 10-2012-7014248.
Korean Office Action dated Sep. 27, 2017 and English translation thereof from corresponding Korean Application No. 10-2012-7014248.
Russian Office Action dated Jan. 12, 2015 from corresponding Russian Application No. 2012120395.
Arde Barinco Inc. (n.d.). Cavitron Reactor Systems, An Efficient Alternative to High-Shear Piston Homogenizers. Retrieved Dec. 9, 2016 from http://www.arde-barinco.com/assets/pdf/Cavitron(S).pdf, 5 pages.
Hall et al., "Capturing Lightning in a Bottle", http://www.pharmpro.com/Articles/2010/07/Capturing-Lightning-In-A-Bottle/, Jul. 16, 2010, 7 pages.
Katchalski et al., "Synthesis of Lysine Anhydride", J.Amer.Chem. Soc. 68, pp. 879-880 (1946).
Kopple et al., "A Convenient Synthesis of 2,5-Piperazinediones", J.Org.Chem. 33(2), pp. 862-864 (1968).
Langhorn et al., "Disperse Difficult Solids", Chemical Engineering, Jul. 2009, pp. 1-5.
Rotor-Stator Generators for Batch, In-Line Mixing (n.d.), Retrieved Oct. 27, 2009 from http://www.ikausa.com/rotor-stator.htm, 3 pages.
Rotor-Stator Technical Information (n.d.), Retrieved Oct. 27, 2009 from http://www.ikausa.com/techinfo.htm, 1 page.
U.S. Appl. No. 13/936,463, filed Jul. 8, 2013, Gandhi et al.
PCT/US2010/055090, Jan. 11, 2011, International Search Report and Written Opinion.
PCT/US2010/055090, May 18, 2012, International Preliminary Report on Patentability.
EP 10827641.1, Nov. 17, 2015, European Search Report.
Russian Office Communication dated Sep. 28, 2018 and English translation thereof in connection with Russian Application No. 2015113474/05.

\* cited by examiner

REACTOR FOR PRODUCING PHARMACEUTICAL PARTICLES IN A PRECIPITATION PROCESS

CROSS REFERENCE TO RELATED APPLICATION

This application is a division of U.S. patent application Ser. No. 13/936,463, filed Jul. 8, 2013, which is a continuation of U.S. patent application Ser. No. 12/917,611, filed Nov. 2, 2010, which claims priority to Provisional Application Ser. No. 61/257,311, filed Nov. 2, 2009, and Provisional Application Ser. No. 61/384,662, filed Sep. 20, 2010, which are hereby incorporated by reference in their entirety.

TECHNICAL FIELD

This invention relates to reactors, reactor systems and methods for producing pharmaceutical particles in a precipitation process during the manufacturing of a drug product. In some embodiments, the reactors, reactor systems and methods are utilized in a process for manufacturing pharmaceutical products for pulmonary delivery.

BACKGROUND

U.S. Pat. No. 6,071,497, issued Jun. 6, 2000 to Steiner et al., describes methods to manufacture microparticles of a diketopiperazine that involves a precipitation of the microparticles. The method described in U.S. Pat. No. 6,071,497, however, is a process in which a drug is incorporated in the microparticles as they form. Alternatively, U.S. Pat. No. 6,444,226 discloses a method for making a formulation using preformed diketopiperazine microparticles by forming a complex of the microparticles with an active agent. Such microparticle suspensions can be further processed to produce dry powder that can be administered to a patient by inhalation for therapeutic purposes. In all of the described methods, precipitation reactions involving diketopiperizine are extremely fast, with a reaction half-time in the order of 0.5 second, and the precipitated suspension is a non-Newtonian fluid.

A precipitation process is typically used to produce small particles, as the crystal formation in the precipitation takes place very rapidly. Conditions used during the precipitation process define the particle size and the structure of the particles. The process involves bringing dissolved solid mixtures to supersaturation while mixing. The mixing rate and level of supersaturation play an important role in particle size formation. Prior art mixing apparatus includes impinging jet mixers, high pressure homogenizers and static mixing followed by spray drying. None of these devices can be used in a continuous process, if the precipitation process is extremely fast and the resulting suspension is a non-Newtonian fluid. The non-Newtonian nature of the fluid causes precipitated particles to stick to the wall of the precipitation device if velocity gradients are small in the exit stream. Thus, clogging of the mixing apparatus can occur.

Accordingly, there is a need for improved reactors, reactor systems and methods for producing particles in a continuous precipitation process.

SUMMARY OF INVENTION

The present invention provides reactors, reactor systems and methods for producing pharmaceutical particles in a precipitation process during the manufacturing of a drug product. The invention is particularly useful for precipitation reactions that occur in a very short time and may cause clogging of a reactor. The invention involves supplying a first reactant material and a second reactant material to the reaction chamber at first and second inlets, respectively. The second inlet may be downstream of the first inlet in the reaction chamber. The first reactant material is increased in speed and is reduced to small droplets and then reacts with the second reactant material downstream of the second inlet to provide at an outlet of the reaction chamber particles formed by reaction of first and second reactant materials.

According to a first aspect of the invention, a reactor is provided for producing particles in a precipitation process. The reactor comprises a housing defining a reaction chamber; a stator assembly including two or more stators in the reaction chamber; a rotor assembly including two or more rotors in the reaction chamber, the rotor assembly configured for rotation about an axis of rotation relative to the stator assembly; a first inlet to supply a first reactant material to the reaction chamber at a first radial location; a second inlet to supply a second reactant material to the reaction chamber at a second radial location different from the first radial location, wherein the first and second reactant materials react to produce precipitation of particles in the reaction chamber; and an outlet to supply the particles formed in the reaction chamber.

According to a second aspect of the invention, a reactor is provided for producing particles in a precipitation process. The reactor comprises a housing enclosing a reaction chamber; a stator assembly including at least a first stator and a second stator in the reaction chamber; a rotor assembly including at least a first rotor, second rotor and a third rotor in the reaction chamber; a first inlet to supply a first reactant material to the reaction chamber upstream of the first rotor; a second inlet to supply a second reactant material to the reaction chamber in a region of the second stator; and an outlet to provide particles formed by reaction of the first and second reactant materials, wherein the first reactant material is increased in speed by the first rotor and is reduced to small droplets by the first stator and the second rotor, and wherein the first reactant material reacts with the second reactant material downstream of the second inlet.

According to a third aspect of the invention, a reactor system is provided for producing particles in a precipitation process. The reactor system comprises a reactor including a housing enclosing a reaction chamber, a stator assembly including at least a first stator and a second stator in the reaction chamber, a rotor assembly including at least a first rotor, a second rotor and a third rotor in the reaction chamber, a first inlet coupled to the reaction chamber upstream of the first rotor, a second inlet coupled to the reaction chamber in a region of the second stator, and an outlet of the reaction chamber; a drive mechanism configured to rotate the rotor assembly relative to the stator assembly in the reaction chamber; a first source configured to supply a first reactant material to the first inlet of the reactor; and a second source configured to supply a second reactant material to the second inlet of the reactor, wherein the first reactant material is increased in speed by the first rotor and is reduced to small droplets by the first stator and the second rotor, and wherein the first reactant material reacts with the second reactant material downstream of the second inlet to provide, at the outlet of the reaction chamber, particles formed by reaction of the first and second reactant materials.

According to a fourth aspect of the invention, a method is provided for producing particles in a precipitation process.

The method comprises providing a reactor having a reaction chamber and including a stator assembly including at least a first stator and a second stator in the reaction chamber and a rotor assembly including at least a first rotor, a second rotor and a third rotor in the reaction chamber; rotating the rotor assembly relative to the stator assembly in the reaction chamber; supplying a first reactant material to the reaction chamber upstream of the first rotor; and supplying a second reactant material to the reaction chamber in a region of the second stator, wherein the first reactant material is increased in speed by the first rotor and is reduced to small droplets by the first stator and the second rotor, wherein the first reactant material reacts with the second reactant material downstream of the second inlet to provide at an outlet of the reaction chamber particles formed by reaction of the first and second reactant materials.

According to a fifth aspect of the invention, a method is provided for producing particles in a precipitation process. The method comprises providing a reactor having a reaction chamber and including a stator assembly having two or more stators and a rotor assembly having two or more rotors; rotating the rotor assembly about an axis of rotation relative to the stator assembly; supplying a first reactant material to the reaction chamber at a first radial location; and supplying a second reactant material to the reaction chamber at a second radial location different from the first radial location, wherein the first and second reactant materials react to produce precipitation of particles in the reaction chamber.

BRIEF DESCRIPTION OF DRAWINGS

For a better understanding of the present invention, reference is made to the accompanying drawings, which are incorporated herein by reference and in which.

DETAILED DESCRIPTION

Figure 1:
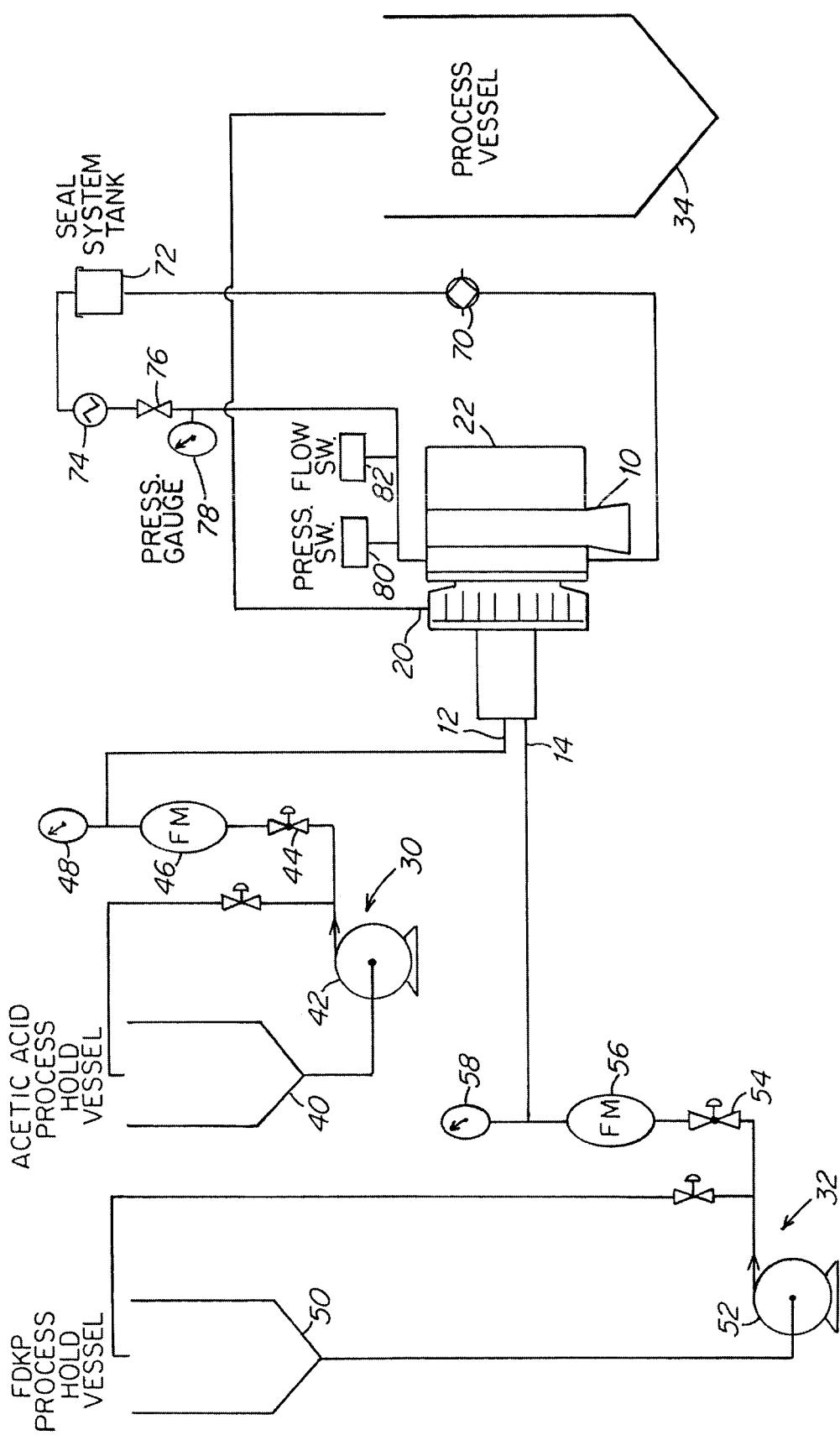
FIG. 1 is a schematic block diagram of a reactor system in accordance with embodiments of the invention.

A schematic block diagram of a reactor system in accordance with embodiments of the invention is shown in FIG. 1. Major components of the reactor system include a reactor 10 having a first inlet 12, a second inlet 14 and an outlet 20. A drive motor 22 is coupled to a rotor assembly of reactor 10. A first source 30 of a first reactant material is coupled to first inlet 12, and a second source 32 of a second reactant material is coupled to second inlet 14. As described below, second inlet 14 includes multiple individual openings into a reaction chamber in reactor 10. Outlet 20 is coupled to a process vessel 34.

As further shown in FIG. 1, first source 30 includes a process hold vessel 40 coupled through a pump 42, a valve 44, and a flow meter 46 to first inlet 12 of reactor 10. A pressure gauge 48 is connected to first inlet 12. Second source 32 includes a process hold vessel 50 coupled through a pump 52, a valve 54 and a flow meter 56 to second inlet 14 of reactor 10. A pressure gauge 58 is connected to second inlet 14. Associated with reactor 10 are a pump 70, a seal system tank 72, a heat exchanger 74, a back pressure valve 76, a pressure gauge 78, a pressure switch 80 and a flow switch 82.

An embodiment of the reactor 10 is shown in FIGS. 2-6. The reactor 10 may be a modification of a commercially available high shear mixer, such as a Cavitron reactor system available from Arde Barinco, Inc. In one specific embodiment, reactor 10 is a modification of a Model 1025 Cavitron reactor system from Arde Barinco, Inc. In the commercially available reactor system, all reactant materials are supplied to the reactor along the axis of rotation, upstream of the stator assembly and the rotor assembly.

Reactor 10 includes a reactor housing 100 which defines a reaction chamber 110. Reactor 10 further includes a rotor assembly 120, as best shown in FIG. 3, and a stator assembly 130, as best shown in FIG. 4. Rotor assembly 120 is configured for rotation about an axis of rotation 132 shown in FIG. 2.

Figure 2:
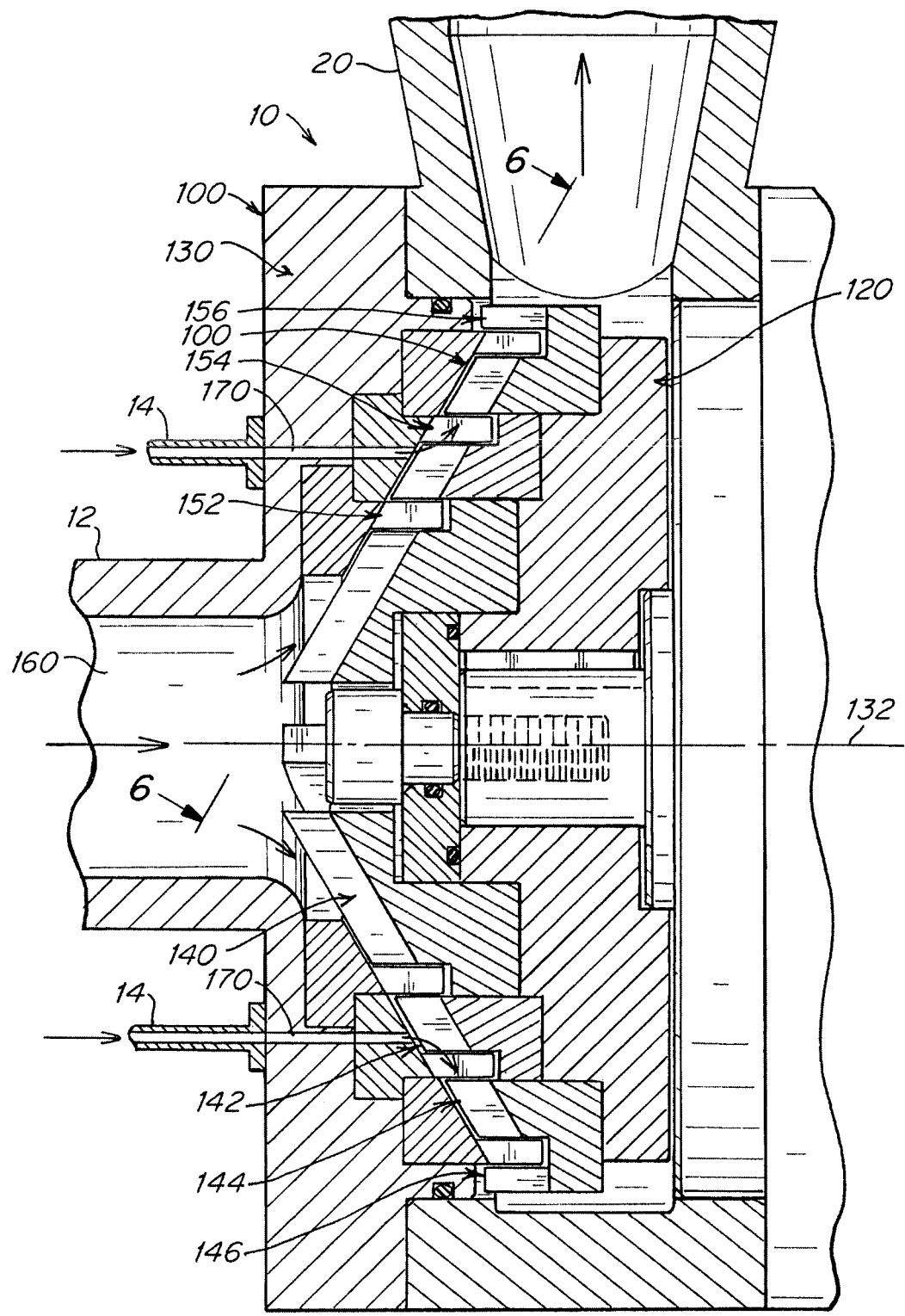
FIG. 2 is a simplified cross-sectional diagram of a reactor in accordance with embodiments of the invention.
Figure 3:
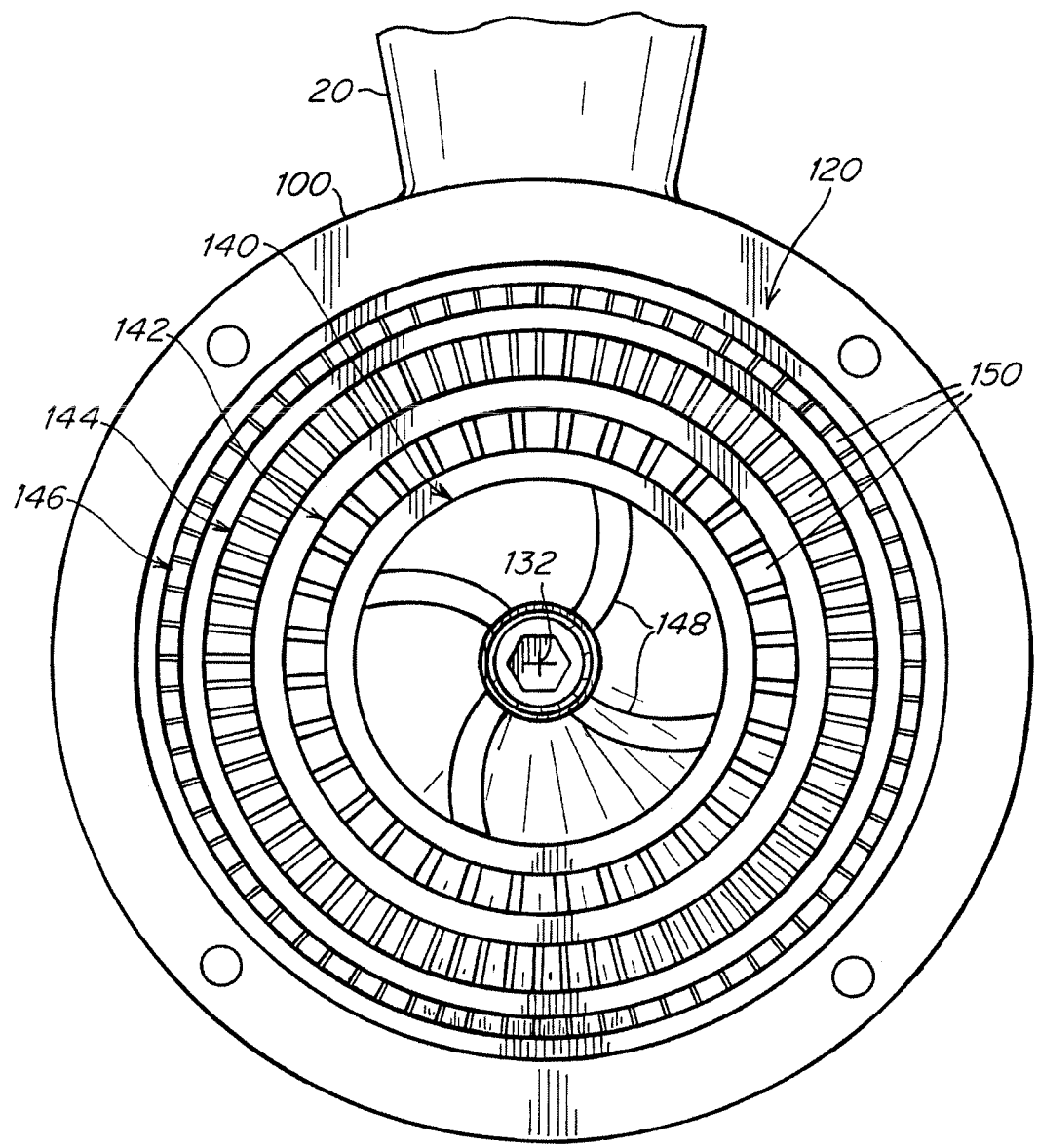
FIG. 3 is a schematic view of a rotor assembly used in a reactor in accordance with embodiments of the invention.
Figure 4:
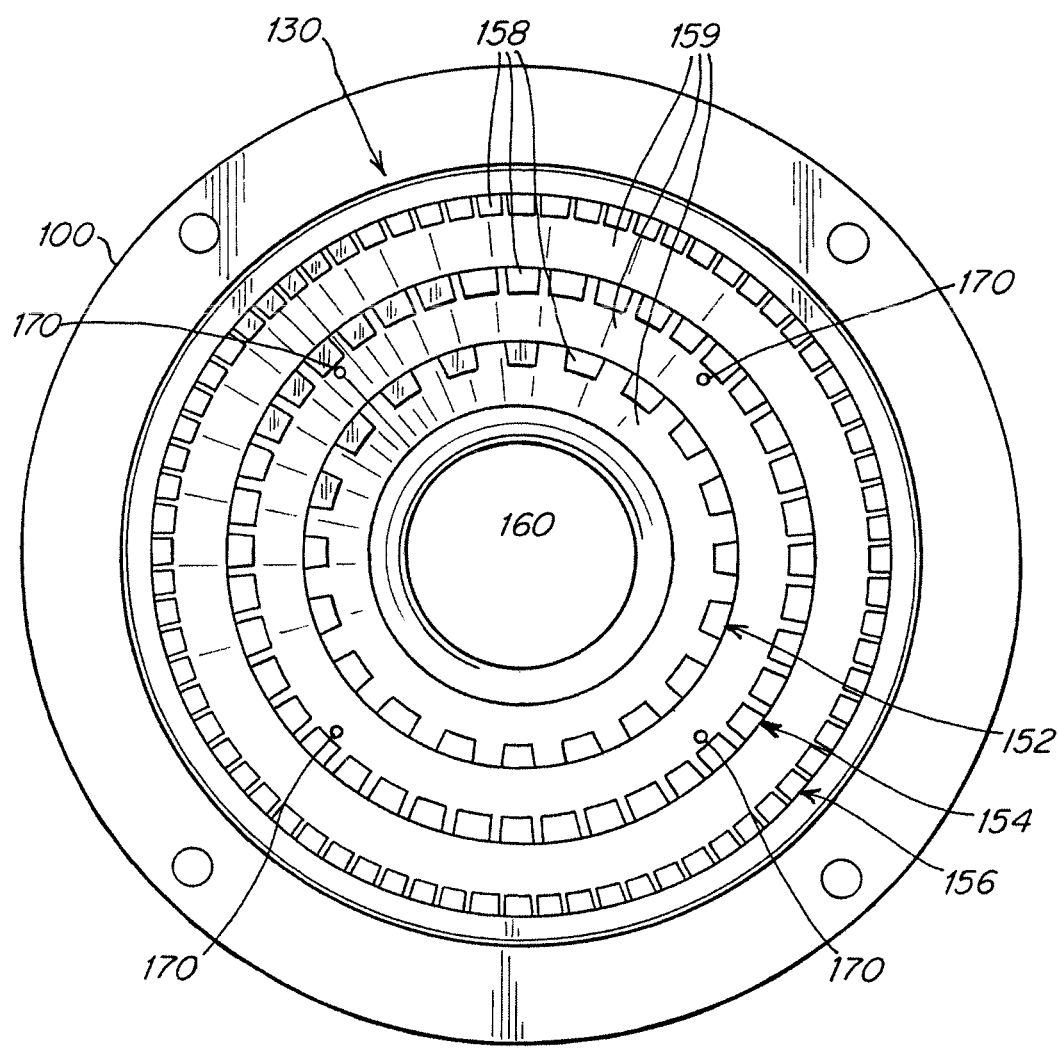
FIG. 4 is a schematic view of a first embodiment of a stator assembly used in a reactor in accordance with embodiments of the invention.
Figure 5:
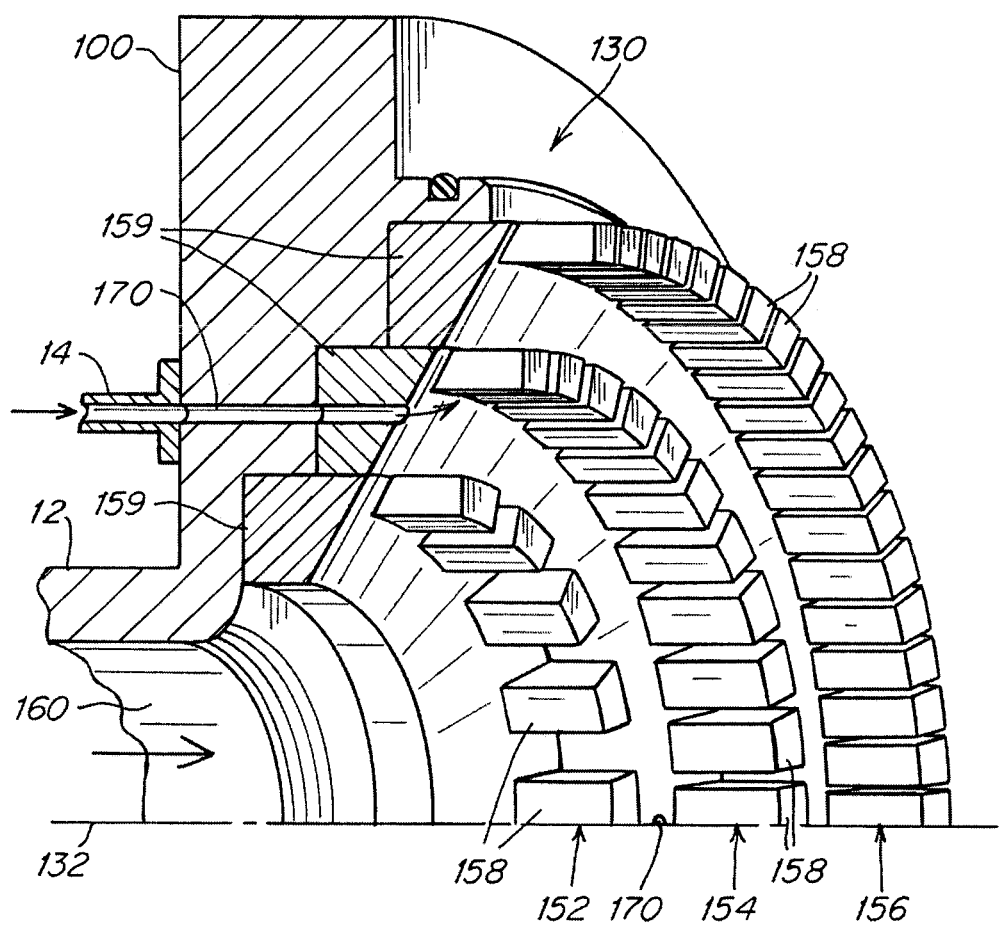
FIG. 5 is a fragmentary cross-sectional schematic view of the stator assembly of FIG. 4.
Figure 6:
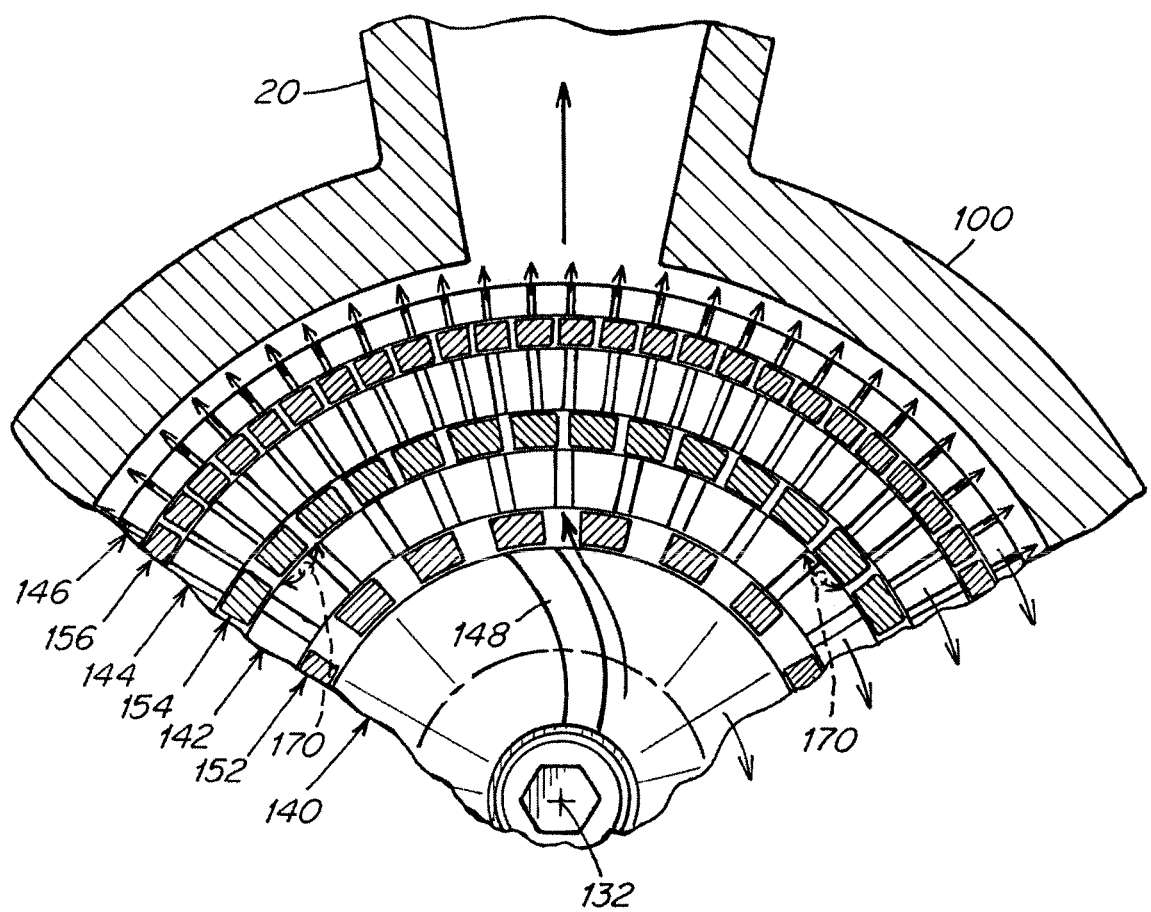
FIG. 6 is a fragmentary cross-sectional schematic view of the reactor system, taken along the line 6-6 of FIG. 2.

Referring to FIGS. 2 and 3, rotor assembly 120 includes a first rotor 140, a second rotor 142, a third rotor 144 and a fourth rotor 146. The first rotor 140 includes an arrangement of generally spiral vanes 148. The second rotor 142, the third rotor 144 and the fourth rotor 146 each include a plurality of spaced-apart teeth 150 arranged in a circular pattern concentric with axis of rotation 132. The first rotor 140, the second rotor 142, the third rotor 144 and the fourth rotor 146 have successively larger diameters, and the circular patterns of teeth 150 are spaced apart in a radial direction.

Referring to FIGS. 2 and 4, in a first embodiment, stator assembly 130 includes a first stator 152, a second stator 154 and a third stator 156, each secured to housing 100. Each stator includes a plurality of spaced apart teeth 158 arranged in a circular pattern concentric with axis of rotation 132. The teeth 158 of each stator may be secured to a ring-shaped base 159. The first stator 152, the second stator 154 and the third stator 156 have successively larger diameters, and the circular patterns of teeth 158 are spaced apart in a radial direction.

When the stator assembly 130 and the rotor assembly 120 are sealed together, the stators and the rotors intermesh so that the first stator 152 is positioned between the first rotor 140 and the second rotor 142; the second stator 154 is positioned between the second rotor 142 and the third rotor 144; and the third stator 156 is positioned between the third rotor 144 and the fourth rotor 146. Rotor assembly 120 is coupled to drive motor 22 (FIG. 1) for rotation of the rotor assembly 120 during operation.

Referring again to FIGS. 2 and 4, first inlet 12 of reactor 10 supplies the first reactant material from first source 30 through an opening 160 to the center of the reaction chamber 110 along axis of rotation 132. Thus, the first reactant material is supplied through first inlet 12 upstream of first rotor 140.

Second inlet 14 of reactor 10 supplies the second reactant material from second source 32 to reaction chamber 110 through a plurality of openings 170 in second stator 154. The openings 170 are located radially inwardly of the teeth 158 of second stator 154 and pass through base 159 of second stator 154. In some embodiments, second inlet 14 may be in fluid communication with four openings 170 in second stator 154. The four openings 170 may be equally spaced from axis of rotation 132 and may be spaced apart by 90° around the circumference of second stator 154. In one example, openings 170 have diameters of ⅛ inch and are located close to the teeth 158 of second stator 154. It is preferred that openings 170 be located in radial alignment with teeth 158 of second stator 154 rather than in alignment with spaces between teeth 158. It will be understood that different sizes, positions and numbers of openings 170 may be utilized within the scope of the invention, based on the requirements of a particular process.

The arrangement of first inlet 12 and second inlet 14 permits the first reactant material supplied through first inlet 12 to be accelerated in velocity and broken down into small droplets before reacting with the second reactant material in the reaction chamber 110. In particular, the first rotor 140 increases the speed of the first reactant material supplied to the reaction chamber 110 through first inlet 112. The first stator 152 and the second rotor 142 convert the first reactant material into small eddies, droplets or globules. The second stator 154 and the third rotor 144 enable reaction of the second reactant material supplied through openings 170 with the first reactant material, which has been increased in speed and converted to small droplets as described above. The reaction produces rapid precipitation of particles in the region of the second stator 154 and the third rotor 144. The third stator 156 and the fourth rotor 146 function to reduce the sizes of relatively large aggregates or agglomerates of particles and produce small diameter, relatively uniform size particles which are supplied through outlet 20 of reactor 10. The reactant materials pass through reaction chamber 110 by passing through the spaces between teeth 150 in second rotor 142, third rotor 144 and fourth rotor 146, and through the spaces between teeth 158 in first stator 152, second stator 154 and third stator 156. The precipitation of particles proceeds continuously without clogging.

Figure 7:
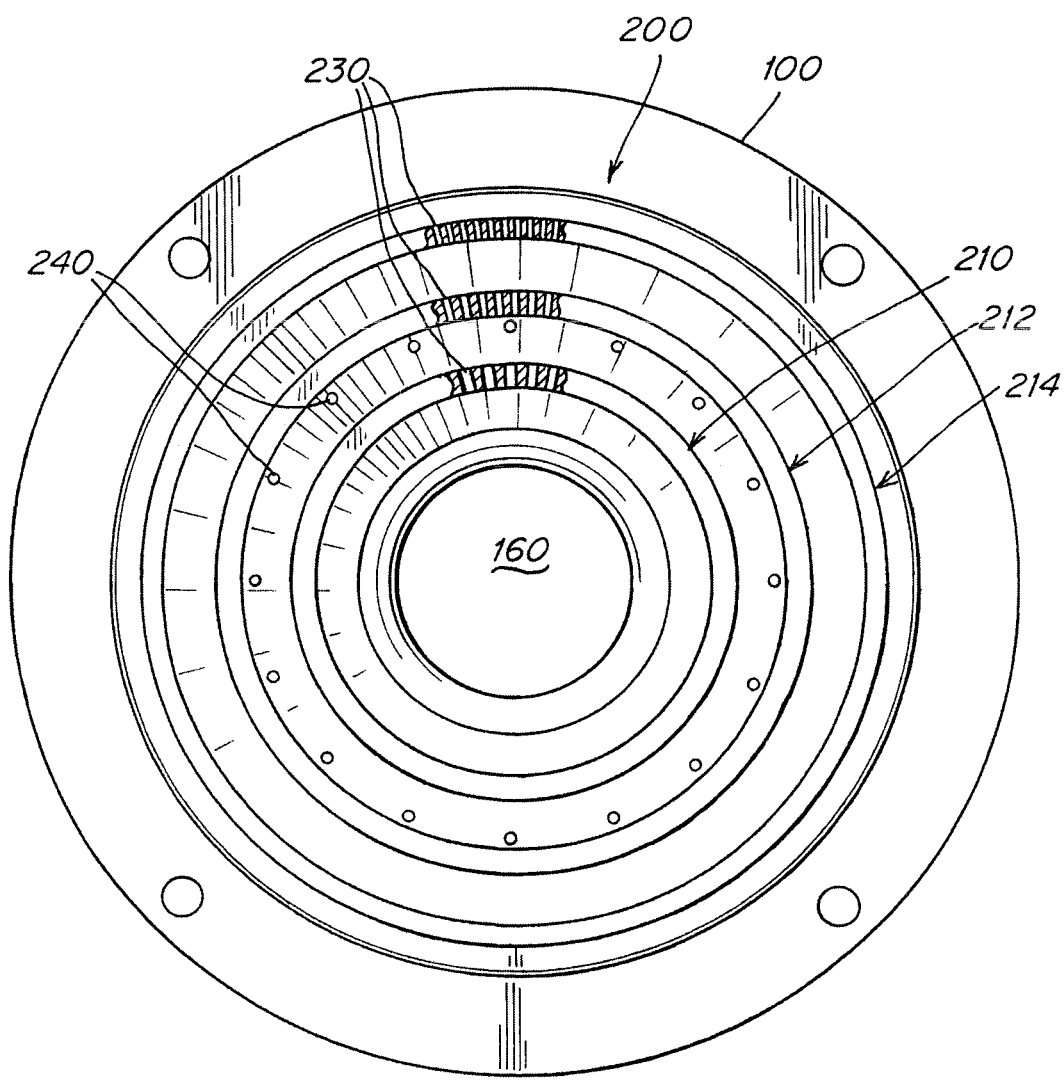
FIG. 7 is a schematic view of a second embodiment of a stator assembly used in a reactor system in accordance with embodiments of the invention.
Figure 8:
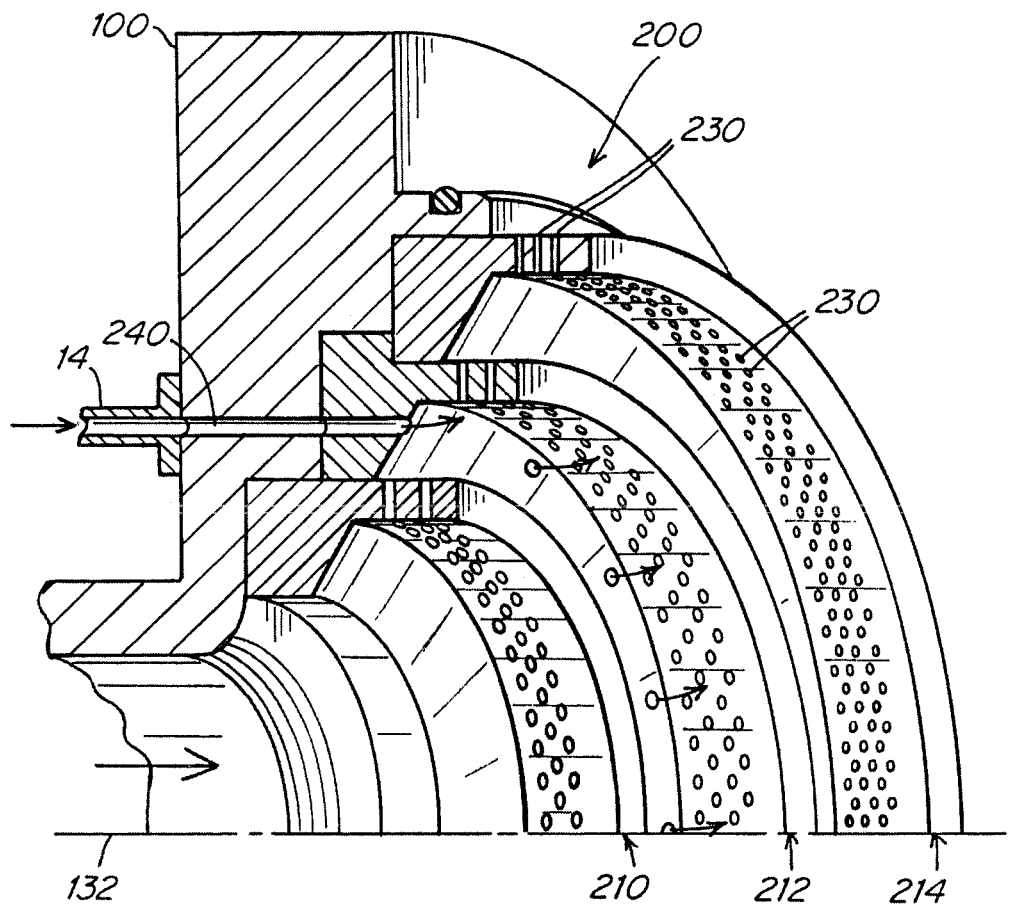
FIG. 8 is a fragmentary cross-sectional schematic view of the stator assembly of FIG. 7.
Figure 8A:
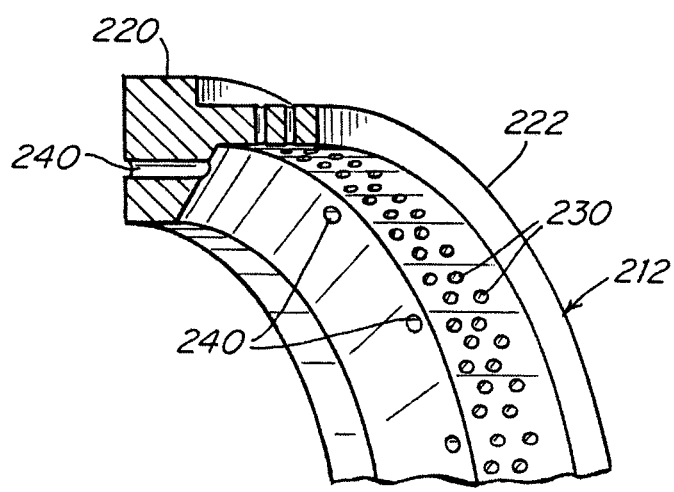
FIG. 8A is a fragmentary cross-sectional schematic view of the second stator of FIG. 8.

A stator assembly 200 in accordance with a second embodiment of the invention is shown in FIGS. 7, 8 and 8A. Stator assembly 200 includes a first stator 210, a second stator 212 and a third stator 214, each secured to housing 100. Each stator may have a circular configuration, including a base 220 and a ring 222 supported by base 220. Each ring 222 includes a plurality of radial nozzles 230 for passing the reactant materials. The nozzles 230 are multiple holes sized to pass the reactant materials. The first stator 210, the second stator 212 and the third stator 214 have successively larger diameters, and the rings 222 of the three stators are spaced apart in a radial direction.

The rotor assembly 120 shown in FIG. 3 and described above may be utilized with stator assembly 200. When the stator assembly 200 and the rotor assembly 120 are sealed together, the stators and the rotors intermesh so that the first stator 210 is positioned between the first rotor 140 and the second rotor 142; the second stator 212 is positioned between the second rotor 142 and the third rotor 144; and the third stator 214 is positioned between the third rotor 144 and the fourth rotor 146.

Second inlet 14 of the reactor supplies the second reactant material from second source 32 to reaction chamber 110 through a plurality of openings 240 in second stator 212. As best shown in FIG. 8A, the openings 240 are located radially inwardly of the ring 222 of second stator 212 and pass through base 220. In some embodiments, second inlet 14 may be in fluid communication with sixteen openings 240 in second stator 212. The sixteen openings 240 may be equally spaced from axis of rotation 132 and may be equally spaced apart around the circumference of second stator 212. In other embodiments, four or eight openings 240 may be provided in second stator 212. Openings 240 may have diameters in a range of about 1/16 inch to ⅛ inch. It will be understood that different sizes, positions and numbers of openings 240 may be utilized within the scope of the invention, based on the requirements of a particular process.

The stator assembly 200 shown in FIGS. 7, 8 and 8A may operate similarly to the stator assembly 130 described above. The reactant materials pass through the reaction chamber 110 by passing through the spaces between teeth 150 in second rotor 142, third rotor 144 and fourth rotor 146, and through the nozzles 230 in first stator 210, second stator 212 and third stator 214. The stator assembly 200 using a configuration of concentric rings provided with nozzles may achieve smaller size particles than the stator assembly 130. Again, the precipitation of particles proceeds continuously without clogging.

Operating parameters that affect the performance of the reactor include, for example, reactor gap settings, pressure of the streams entering the reactor, temperature of the streams entering the reactor, mass flow rate of streams entering the reactor, rotating speed of the rotor assembly, and residence time in the reactor. Furthermore, rotor and stator parameters, such as the number of teeth in the rotors and stators and the gaps between the teeth of the rotors and stators, affect performance.

In a specific process, the reactor system is used to manufacture microparticles of a diketopiperizine for pharmaceutical applications. In particular embodiments, the diketopiperizine may be (bis-3,6-(N-fumaryl-4-aminobutyl)-2,5-diketo-diketopiperazine, also known as fumaryl diketopiperizine (FDKP). In particular, the microparticles are processed to produce a dry powder that can be administered to a patient by inhalation for therapeutic purposes. In this process, the first reactant material, supplied through first inlet 12 from first source 30, is an acid such as acetic acid with or without a surfactant; such as polysorbate 80 in a concentration of from about 0.01% to about 5% (v/v). The second reactant material, supplied through second inlet 14 from second source 32, is an FDKP solution, optionally containing a surfactant of from about 0.01% to about 5% (v/v) in the solution. The reactor 10 produces microparticles, known as TECHNOSPHERE® microparticles. In certain embodiments, the reaction can take place without containing surfactant.

In one embodiment, the process of making the particles includes: (1) an FDKP solution including liquid-like globules, contacts an acetic acid solution in a micro level, (2) a basic FDKP solution reacts with the acetic acid, (3) the reaction forces the FDKP molecules to precipitate out of the solution, and (4) the FDKP molecules combine with each other and form TECHNOSPHERE particles. In order to make small particles of the required particle size requires very small globules of the FDKP and basic solutions which results in very efficient mixing, and faster precipitation of FDKP molecules. The faster the molecules form, the more FDKP molecule sites are available to attach to. Thus, large numbers of small TECHNOSPHERE particles form in the region of second stator 154 and third rotor 144. Third stator 156 and fourth rotor 146 function as a shearing device which breaks down larger TECHNOSPHERE particles formed in the process. As a result very uniform particle size distribution is obtained.

A process for large scale manufacturing of FDKP microparticles, greater than 500 grams, for use in a dry powder formulation for pulmonary delivery is now described. The process uses a reactor for facilitating the mixing of solutions so that microparticles precipitate out of solution forming an FDKP suspension upon providing a high intensity micromixing environment. The process comprises: preparing a first solution comprising an acid such hydrochloric acid and glacial acetic acid in a vessel having about at least 10 liter capacity; preparing a second solution comprising diketopiperazine in a base such as ammonium hydroxide or sodium hydroxide at a pH greater than about 10; feeding, for example, by pumping the first solution and the second solution at a predetermined flow rate and temperature to a reactor so that the first solution and the second solution collide at an entrance of the reactor; wherein the microparticles form by high energy dissipation within the reactor. The process can further comprise feeding a third solution or a fourth solution, including deionized water into the reactor which is utilized for washing and removing the unreacted components of the first and second solutions to yield a substantially pure composition of microparticles in a suspension. The process is a continuous process and the microparticles in suspension are collected in a third vessel downstream from the reactor. Microparticles formed using the instant process can have a median aerodynamic diameter of approximately 2-2.5 μm, high internal porosity, and a large surface that can be used for the adsorption of peptides, proteins or other drugs or active ingredients. The instant process can be controlled to generate larger particle sizes depending on their use by adjusting the reaction conditions such as the speed of the reaction and flow rates of the solutions. For example, for nasal delivery, particle sizes greater than 10 μm or greater than 20 μm can be made.

In one embodiment, A process for manufacturing diketopiperazine microparticles, comprising: preparing a first solution comprising an acid in a vessel having about at least 10 liter capacity; preparing a second solution comprising a diketopiperazine dissolved in a solution having a pH greater than about 10; pumping the first solution and the second solution at a predetermined flow rate and temperature into a high shear mixer or reactor so that the first solution and the second solution collide inside the reactor to form a precipitate; mixing the first solution and the second solution at flow rate to yield an acid to base ratio of about 0.8 to about 1.2.

As used herein, the term "microparticle" refers to a particle with a diameter of about 0.5 to about 1000 μm, irrespective of the precise exterior or interior structure. Microparticles having a diameter of between about 0.5 and about 10 microns can reach the lungs, successfully passing most of the natural barriers. A diameter of less than about 10 microns is required to navigate the turn of the throat and a diameter of about 0.5 microns or greater is required to avoid being exhaled. To reach the deep lung (or alveolar region) where most efficient absorption is believed to occur, it is preferred to maximize the proportion of particles contained in the "respirable fraction" (RF), generally accepted to be about 0.5 to about 5.7 microns, though some references use somewhat different ranges.

As used herein, the term "dry powder" refers to a fine particulate composition that is not suspended or dissolved in a propellant, carrier, or other liquid. It is not meant to necessarily imply a complete absence of all water molecules.

As used herein, the term "about" is used to indicate that a value includes the standard deviation of the measurement for the device or method being employed to determine the value.

Diketopiperazines

One class of drug delivery agents that has been used to overcome problems in the pharmaceutical arts such as drug instability and/or poor absorption are the 2,5-diketopiperazines. 2,5-Diketopiperazines are represented by the compound of the general Formula 1 as shown below wherein $E_1$ and $E_2$ are independently N or more particularly NH. In other embodiments, $E_1$ and/or $E_2$ are independently an oxygen or a nitrogen so that wherein either one of the substituents for $E_1$ and $E_2$ is an oxygen and the other is a nitrogen the formula yields the substitution analog diketomorpholine, or when both $E_1$ and $E_2$ are oxygen the formula yields the substitution analog diketodioxane.

Formula 1

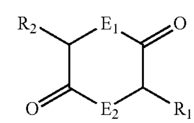

These 2,5 diketopiperazines have been shown to be useful in drug delivery, particularly those bearing acidic $R_1$ and $R_2$ groups as described in, for example, U.S. Pat. No. 5,352,461 entitled "Self Assembling Diketopiperazine Drug Delivery System;" U.S. Pat. No. 5,503,852 entitled "Method For Making Self-Assembling Diketopiperazine Drug Delivery System;" U.S. Pat. No. 6,071,497 entitled "Microparticles For Lung Delivery Comprising Diketopiperazine;" and U.S. Pat. No. 6,331,318 entitled "Carbon-Substituted Diketopiperazine Delivery System," each of which is incorporated herein by reference in its entirety for all that it teaches regarding diketopiperazines and diketopiperazine-mediated drug delivery. Diketopiperazines can be formed into microparticles that incorporate a drug or microparticles onto which a drug can be adsorbed. The combination of a drug and a diketopiperazine can impart improved drug stability and/or absorption characteristics. These microparticles can be administered by various routes of administration. As dry powders these microparticles can be delivered by inhalation to specific areas of the respiratory system, including the lungs.

Methods for synthesizing diketopiperazines are described in, for example, Katchalski, et al., J. Amer. Chem. Soc. 68, 879-880 (1946) and Kopple, et al., J. Org. Chem. 33(2), 862-864 (1968), the teachings of which are incorporated herein by reference in their entirety. 2,5-Diketo-3,6-di(aminobutyl)piperazine (Katchalski et al. refer to this as lysine anhydride) can also be prepared via cyclodimerization of N-ε-P-L-lysine in molten phenol, similar to the Kopple method, followed by removal of the blocking (P)-groups with an appropriate reagent and conditions. For example, CBz-protecting groups can be removed using 4.3 M HBr in acetic acid. This route can be preferred because it uses a commercially available starting material, it involves reaction conditions that are reported to preserve stereochemistry of the starting materials in the product and all steps can be easily scaled up for manufacture. Methods for synthesizing diketopiperazines are also described in U.S. Pat. No. 7,709,639, entitled, "Catalysis of Diketopiperazine Synthesis," which is also incorporated by reference herein for its teachings regarding the same.

Fumaryl diketopiperazine (bis-3,6-(N-fumaryl-4-aminobutyl)-2,5-diketo-diketopiperazine; FDKP) is one preferred diketopiperazine for pulmonary applications:

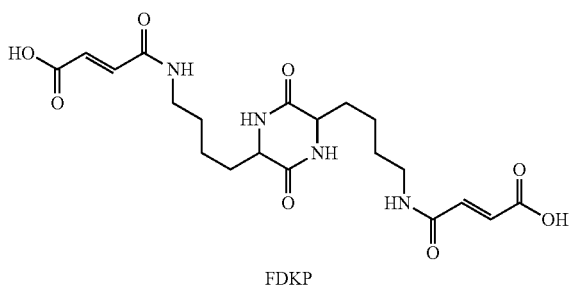

FDKP

FDKP provides a beneficial microparticle matrix because it has low solubility in acid but is readily soluble at neutral or basic pH. These properties allow FDKP to crystallize and the crystals to self-assemble into form microparticles under acidic conditions. The particles dissolve readily under physiological conditions where the pH is neutral. As noted, microparticles having a diameter of between about 0.5 and about 10 microns can reach the lungs, successfully passing most of the natural barriers. Particles in this size range can be readily prepared from FDKP.

In one embodiment, the process comprises mixing an acidic solution with a basic solution containing a predetermined amount of dissolved FDKP solute using a high shear or high intensity mixer or homogenizer as described herein. In this setup, the homogenizer is provided with at least two inlet ports, one, the first inlet port which is connected to a first vessel for providing a first solution such as the acid, including glacial acetic acid or hydrochloric acid contained from the first vessel; a second inlet port connected to a second vessel containing and for providing the FDKP solution in a base. The solutions can be fed through the ports each at a predetermined flow rate so that they are mixed in the high shear mixer to precipitate the FDKP microparticles out of solution forming a suspension. In certain embodiments, the solutions can be fed into the reactor at a flow rate of about 10 kg/min to about 100 kg/min, or from about 15 kg/min to about 35 kg/min. The process for making FDKP microparticles is a continuous process so that the suspension flows out of the reactor through an outlet port and into a third vessel for further processing such as further washing of the suspension prior to the adsorption step of an active agent. In certain embodiments, the pressure at which the reaction can be carried out can range from about 15 psig to about 2,000 psig depending on the high shear mixer used. In one embodiment, the pressure at which the reaction can be carried out can range from about 35 psig to about 110 psig.

In certain embodiments, the process for making FDKP microparticles is accomplished by changing the parameters associated with supersaturation and temperature of crystallization, for example, using equipment specific parameters related to hydrodynamics of the precipitation device which must remain constant. In some embodiments, the degree of supersaturation can be changed by varying the mixing ratio of the acid and base feed solutions in the reactor or homogenizer, and the crystallization temperature can be changed by varying feed solution temperature. In an exemplary embodiment, the temperature of the reaction can range from about 10° C. to about 30° C.; from about 13° C. to about 27° C., or from about 15° C. to about 20° C.

In an exemplary embodiment, the FDKP solution is a basic solution having a pH greater than pH 10. Suitable bases for use in the basic solution can be ammonium hydroxide, sodium hydroxide, potassium hydroxide and the like. In this and other embodiment, the acidic solution comprises glacial acetic acid in an amount varying from about 1% to about 4% (w/w). Other acids can be used in the reaction, for example, hydrochloric acid. In particular embodiments, the acid to base ratio of the reaction can vary from about 0.8 to about 1.2 (w/w) or from about 0.95 to about 1.05. The manufacturing process for making FDKP microparticles can vary depending in amount of the starting materials stored in the vessels. For example, vessel 1 and vessel 2 can vary in size and can be loaded with, for example, from about 10 L to about 10,000 L of solution or higher depending on the manufacturing needs.

Microparticles made by the present manufacturing process under the parameters outlined above are suitable for use with a variety of active agents including, but not limited to peptides such as endocrine hormones, including insulin, glucagon, glucagon-like peptide 1, proteins, nucleic acids, and the like. The microparticles so produced are in particular suitable for use with active agents that can be delivered by way of the lungs or by pulmonary delivery, and for oral inhalation with dry powder inhalation systems.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A reactor for producing particles in a precipitation process, comprising:
   a housing defining a reaction chamber;
   a stator assembly including a first stator and a second stator in the reaction chamber;
   a rotor assembly including two or more rotors in the reaction chamber, the rotor assembly configured for rotation about an axis of rotation relative to the stator assembly;
   a first inlet to supply a first reactant material to the reaction chamber at a first radial location;
   a second inlet to supply a second reactant material to the reaction chamber at a second radial location different from the first radial location, wherein the first and second reactant materials react to produce precipitation of particles in the reaction chamber; and
   an outlet to supply the particles formed in the reaction chamber, wherein each of the first stator and the second stator includes a plurality of circumferentially spaced teeth, wherein the second inlet includes openings in the stator assembly, wherein the openings are located radially inwardly of and in radial alignment with respective teeth of the second stator and wherein the openings are in radial alignment with respective gaps between teeth of the first stator.

2. A reactor as defined in claim 1, wherein the rotor assembly includes at least a first rotor, a second rotor and a third rotor, wherein the first inlet is positioned to supply the first reactant material to the reaction chamber upstream of the first rotor, and wherein the second inlet is positioned to supply the second reactant material to the reaction chamber in a region of the second stator.

3. A reactor as defined in claim 2, wherein the stator assembly further includes a third stator and the rotor assembly further includes a fourth rotor, and wherein the third stator and the fourth rotor reduce the sizes of particles formed by reaction of the first and second reactant materials.

4. A reactor as defined in claim 1, wherein the second inlet comprises a plurality of openings in communication with the reaction chamber, the openings spaced from an axis of the rotor assembly.

5. A reactor as defined in claim 1, wherein the second inlet comprises four openings, the four openings being equally spaced from an axis of rotation and spaced apart by 90° around said one stator.

6. A reactor system for producing particles in a precipitation process, comprising:
   a reactor including a housing enclosing a reaction chamber, a stator assembly including at least a first stator and a second stator in the reaction chamber, a rotor assembly including at least a first rotor, a second rotor and a third rotor in the reaction chamber, a first inlet coupled to the reaction chamber upstream of the first rotor, a second inlet coupled to the reaction chamber in a region of the second stator, and an outlet of the reaction chamber;
   a drive mechanism configured to rotate the rotor assembly relative to the stator assembly in the reaction chamber;
   a first source configured to supply a first reactant material to the first inlet of the reactor; and
   a second source configured to supply a second reactant material to the second inlet of the reactor, wherein the first reactant material is increased in speed by the first rotor and is reduced to small droplets by the first stator and the second rotor, wherein the first reactant material reacts with the second reactant material downstream of the second inlet to provide, at the outlet of the reaction chamber, particles formed by reaction of the first and second reactant materials, wherein each of the first stator and the second stator includes a plurality of circumferentially spaced teeth, wherein the second inlet includes openings in the stator assembly, wherein the openings are located radially inwardly of and in radial alignment with respective teeth of the second stator and wherein the openings are in radial alignment with respective gaps between teeth of the first stator.

7. A reactor system as defined in claim 6, wherein the first source includes a first process hold vessel coupled through a first pump to the first inlet of the reactor.

8. A reactor system as defined in claim 7, wherein the second source includes a second process hold vessel coupled through a second pump to the second inlet of the reactor.

\* \* \* \* \*